(12) United States Patent
Liu et al.

(10) Patent No.: US 8,623,400 B2
(45) Date of Patent: Jan. 7, 2014

(54) DRUG-CARRYING CONTACT LENS AND METHOD FOR FABRICATING THE SAME

(75) Inventors: Dean-Mo Liu, Hsinchu County (TW); Pei-Ling Liu, Changhua County (TW)

(73) Assignee: National Chiao Tung University, Hsinchu (TW)

( * ) Notice: Subject to any disclaimer, the term of this patent is extended or adjusted under 35 U.S.C. 154(b) by 0 days.

(21) Appl. No.: 13/269,005

(22) Filed: Oct. 7, 2011

(65) Prior Publication Data

US 2013/0011460 A1      Jan. 10, 2013

(30) Foreign Application Priority Data

Jul. 8, 2011   (TW) .............................. 100124215 A

(51) Int. Cl.
*A61K 9/00* (2006.01)
(52) U.S. Cl.
USPC .......................................... 424/429; 424/427
(58) Field of Classification Search
None
See application file for complete search history.

(56) References Cited

U.S. PATENT DOCUMENTS

| | | |
|---|---|---|
| 2002/0018732 A1 | 2/2002 | Hung et al. |
| 2002/0177577 A1 | 11/2002 | Hung et al. |
| 2002/0197300 A1 | 12/2002 | Schultz et al. |
| 2003/0203001 A1 | 10/2003 | Schultz |
| 2004/0121924 A1 | 6/2004 | Hong et al. |
| 2004/0127461 A1 | 7/2004 | Hung et al. |
| 2004/0241207 A1 | 12/2004 | Chauhan et al. |
| 2005/0058844 A1 | 3/2005 | Rubner et al. |
| 2005/0079195 A1* | 4/2005 | Kataoka et al. ............... 424/423 |
| 2005/0085758 A1 | 4/2005 | Schultz |
| 2005/0196428 A1 | 9/2005 | Schultz |
| 2006/0287278 A1 | 12/2006 | Hu et al. |
| 2008/0038353 A1* | 2/2008 | Lavasanifar et al. .......... 424/486 |
| 2008/0124378 A1 | 5/2008 | Byrne et al. |

(Continued)

FOREIGN PATENT DOCUMENTS

| | | |
|---|---|---|
| CN | 201012180 Y | 1/2008 |
| CN | 101293963 A | 10/2008 |

(Continued)

OTHER PUBLICATIONS

Lui et al. Chitosan Silica complex membranes from sulfonic acid functionalized silica nanoparticles for perforation dehydration of ethanol water solutions, Biomacromolecules, 2005, 6, 368-373.*

(Continued)

*Primary Examiner* — Anand Desai
*Assistant Examiner* — Melissa Mercier
(74) *Attorney, Agent, or Firm* — Muncy, Geissler, Olds & Lowe, PLLC

(57) ABSTRACT

The present invention discloses a drug-carrying contact lens and a method for fabricating the same. The drug-carrying contact lens comprises a contact lens containing at least one amphiphatic hybrid nanocarrier carrying drug molecules. According to the heat or light sensitivity of the drug molecule, the present invention respectively fabricates an encapsulation-type drug-carrying contact lens and a drug-soaking type drug-carrying contact lens. The present invention uses a highly-biocompatible amphiphatic hybrid nanocarriers having superior drug encapsulation capability to wrap the drug molecules. Thereby, the drug molecules are uniformly distributed in the contact lens and can be gradually and locally released to the eye of the user wearing the contact lens. Therefore, the present invention can prevent or cure ocular diseases with the loss and side effects of the drug being reduced.

5 Claims, 7 Drawing Sheets
(1 of 7 Drawing Sheet(s) Filed in Color)

(56) References Cited

U.S. PATENT DOCUMENTS

| | | |
|---|---|---|
| 2009/0200692 A1 | 8/2009 | Chang |
| 2009/0201465 A1 | 8/2009 | Huth |
| 2010/0113901 A1 | 5/2010 | Zhang et al. |
| 2010/0330146 A1 | 12/2010 | Chauhan et al. |
| 2012/0153520 A1 | 6/2012 | Liu et al. |

FOREIGN PATENT DOCUMENTS

| | | |
|---|---|---|
| CN | 101344648 A | 1/2009 |
| EP | 0486294 A2 | 5/1992 |
| EP | 0882996 A2 | 9/1998 |
| GB | 2273102 A | 8/1994 |
| JP | 1265224 A | 10/1989 |
| JP | 4230636 A | 8/1992 |
| JP | 5142502 A | 6/1993 |
| JP | 7218878 A | 8/1995 |
| JP | 7223966 A | 8/1995 |
| JP | 2002226503 A | 8/2002 |
| JP | 2005215111 A | 8/2005 |
| JP | 2005250321 A | 9/2005 |
| JP | 2007167358 A | 7/2007 |
| KR | 20050037992 A | 4/2005 |
| MX | PA05006631 A | 8/2005 |
| TW | I227673 | 2/2005 |
| WO | WO 94/13774 A1 | 6/1994 |
| WO | WO 2004/061063 A1 | 7/2004 |
| WO | WO 2007/002345 A2 | 1/2007 |
| WO | WO 2008/060574 A2 | 5/2008 |
| WO | WO 2008/005276 A2 | 10/2008 |
| WO | WO 2008/137863 | 11/2008 |
| WO | WO 2008/151019 A1 | 12/2008 |
| WO | WO 2010/068281 | 6/2010 |
| WO | WO 2010/095478 A1 | 8/2010 |

OTHER PUBLICATIONS

Galan, et al., "Methyl Trypsin Loaded Poly(D,L-Lactide-Coglycolide) Nanoparticles for Contact Lens Care", Journal of Pharmaceutical Sciences, (Mar. 2010), pp. 1414-1426, vol. 99, No. 3.

Kim, et al., "Extended Release of Dexamethasone from Silicone-Hydrogel Contact Lenses Containing Vitamin E", Journal of Controlled Release, (2010), pp. 110-116, vol. 148.

Gupta, et al., "Drug Transport in HEMA Conjunctival Inserts Containing Precipitated Drug Particles", Journal of Colloid and Interface Science, (2010) pp. 31-42, vol. 347.

Schultz, et al., "Contact Lenses as a Drug Delivery Device for Epidermal Growth Factor in the Treatment of Ocular Wounds", Clinical and Experimental Optometry, (2010), pp. 61-65, vol. 93.

Gulsen, et al., "Dispersion of microemulsion drops in HEMA hydrogel: a potential ophthalmic drug delivery vehicle", International Journal of Pharmaceutics, vol. 292, No. 1-2, Mar. 23, 2005, pp. 95-117.

Tung, Tsan-Hua, "Amphiphilic Chitosan—Crystalline Silica Hybrid Macromolecules: Molecular Design, Self-Assembly Behavior, and Drug Recovery", Submitted to Department of Material Science and Engineering—College of Engineering, Apr. 2010 (8 pages).

* cited by examiner

- : hydrophilic silanol group ( II )
- : hydrophobic hexanoyl group ( III )
- ~ : main chain of chitosan ( I )

DRUG-CARRYING CONTACT LENS AND METHOD FOR FABRICATING THE SAME

BACKGROUND OF THE INVENTION

1. Field of the Invention

The present invention relates to a drug eluting technology in contact lens, particularly to a drug-carrying contact lens that can release drugs locally for a long period of time and a method for fabricating the same.

2. Description of the Related Art

Many people suffer from damaged or degenerating eyesight, such as myopia. Normally, the nearsighted wears glasses or contact lenses to obtain clear vision. For some people, the contact lens is a favorable option.

The contact lenses may be categorized into the rigid contact lens and the soft contact lens. The soft contact is normally made of silicone hydrogels, PAA (polyacrylamide), or PHEMA (poly 2-Hydroxy ethylmethacrylate). The soft contact lens is more comfortable and cheaper for the users and thus becomes the mainstream in the market. Although the material of the soft contact lens has been greatly improved, the irritation problem of wearing contact lenses still exists. The user wearing contact lenses usually feels eyes dry and irritable because humidity decreases in user's eyes. Thus, the user has to apply a wetting agent to the contact lenses. When infected or irritated, eyes need some eyedrops or refreshing liquids. However, most of eyedrops or refreshing liquids are unlikely to apply to the eyes wearing contact lenses. In such a condition, the users should feel very inconvenient.

No matter whether the user wears contact lenses or not, the eyedrop, which has been dropped into eyes, would lose because of blinking, dilution, or rejection. Thus, the eyes can only absorb about 5% of the drug. Besides, the drug stays in eyes only for a short period of time. Once the drug enters the blood circulation, some side effects may occur.

Accordingly, the present invention proposes a drug-carrying contact lens and a method for fabricating the same to prevent or cure ocular diseases and overcome the abovementioned problems.

SUMMARY OF THE INVENTION

The primary objective of the present invention is to provide a drug-carrying contact lens and a method for fabricating the same, wherein a high biocompatibility nanocarrier having superior drug encapsulation capability is used to wrap drugs or absorb drug molecules from a drug solution and make the drugs uniformly distributed in a contact lens, whereby the contact lens can locally release the drugs to the eyes to prevent or cure ocular diseases.

Another objective of the present invention is to provide a drug-carrying contact lens and a method for fabricating the same, wherein the drug molecules carried by the contact lens can be gradually released to the tissue of the eye for a pong period of time (>24 hours), whereby are minimized the loss and side effects of the drug.

A further objective of the present invention is to provide a facile method for fabricating a drug-carrying contact lens.

To achieve the abovementioned objectives, the present invention proposes a drug-carrying contact lens, which comprises a contact lens containing at least one amphiphatic hybrid nanocarrier carrying drug molecules, whereby the drug molecules are encapsulated within the hybrid nanocarriers and uniformly distributed throughout the contact lens.

The amphiphatic hybrid nanocarrier is an amphiphatic organic-inorganic chitosan-silica hybrid nanocarrier.

In one embodiment, the method of the present invention comprises steps: adding amphiphatic hybrid nanocarriers to a drug solution, and agitating them into a uniform first mixture solution; fully mixing the first mixture solution with a contact lens material to form a second mixture solution, and pouring the second mixture solution into at least one mold; light-curing the second mixture solution in the mold, and demolding the cured second mixture solution to obtain a first encapsulation-type drug-carrying contact lens.

In another embodiment, the method of the present invention comprises steps: mixing a drug solution, an amphiphatic hybrid nanocarrier and a contact lens material, and agitating them into a uniform third mixture solution; spraying the third mixture solution onto the surface of a contact lens to form a film on the surface of contact lens, covered either all or part of the surface of a given contact lens; and obtain a second encapsulation-type drug-carrying contact lens.

In a further embodiment, the method of the present invention comprises steps: mixing an amphiphatic hybrid nanocarrier and a contact lens material, and agitating them into a uniform fourth mixture solution; pouring the fourth mixture solution into at least one mold, light-curing the fourth mixture solution, and demolding the cured fourth mixture solution to obtain a nanocarrier-containing contact lens; soaking the nanocarrier-containing contact lens in a drug solution until concentration reaches a dynamic equilibrium to obtain a drug-soaking type drug-carrying contact lens.

Below, the embodiments are described in detail in cooperation with the attached drawings to make easily understood the objectives, technical contents, characteristics and accomplishments of the present invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 7($b$) shows the drug release test result of the drug-carrying contact lenses of the present invention respectively containing different concentrations of Vitamin B12;

DETAILED DESCRIPTION OF THE INVENTION

Figure 1:
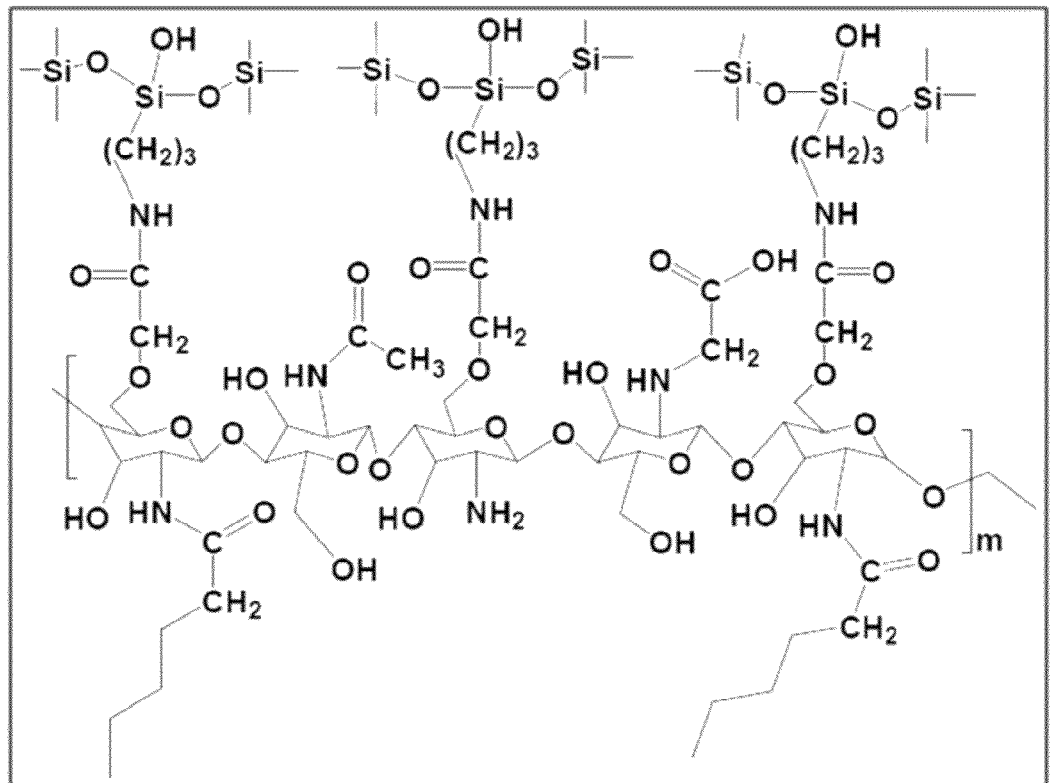
FIG. 1 schematically shows the structural formula of an amphiphatic organic-inorganic chitosan-silica hybrid nanocarrier and the self-assembly thereof according to one embodiment of the present invention.
Figure 1:
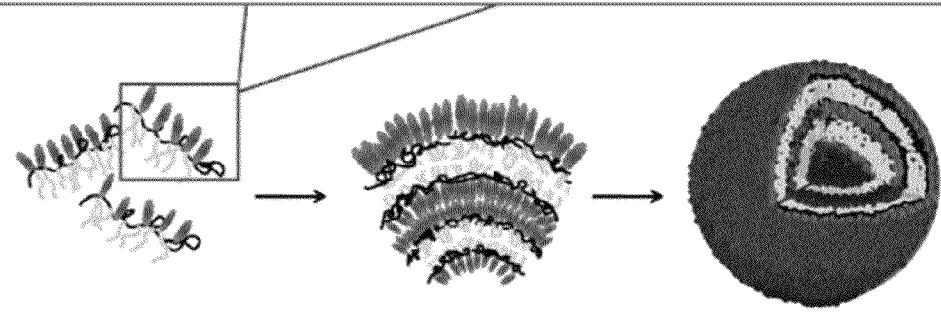

The present invention pertains to a local drug delivery technology, wherein a contact lens releases a drug locally to prevent or cure ocular diseases. In the present invention, a high biocompatible nanocarrier having superior drug-encapsulation capability wraps and carries a drug, and uniformly distributed in a contact lens. The contact lens can gradually release the drug to the eye for a reasonably long period of time (>24 hours), whereby are minimized the loss and side effects of the drug.

The drug-carrying contact lens of the present invention comprises a contact lens containing at least one amphiphatic hybrid nanocarrier. The amphiphatic hybrid nanocarrier carries hydrophilic or hydrophobic drug molecules. The amphiphatic hybrid nanocarriers and the drug molecules carried by the amphiphatic hybrid nanocarriers are distributed throughout the contact lens or on the surface of the contact lens. The amphiphatic hybrid nanocarrier is an optically transparent, in visible region, nanosphere having a diameter of 20-300 nm. The amphiphatic hybrid nanocarriers with a concentration of 0.01-5 wt % in a contact lens were fabricated. The drugs carried by the amphiphatic hybrid nanocarriers included Vitamin A, Vitamin B12, Vitamin C, Vitamin E, azithromycin, fluorometholone facetate, bacitracin, neomycin, polymyxin B sulfate, Oxytetracycline HCl, erythromycin, dexamethasone, prednisolone acetate, timolol maleate, or hydrocortisone.

In one embodiment, the amphiphatic hybrid nanocarrier is an amphiphatic organic-inorganic chitosan-silica hybrid nanocarrier. The chitosan used by the present invention is a biocompatible material and has been widely used in biomedical-related applications. The present invention modifies chitosan into an amphiphatic organic-inorganic nanocarrier (silica-CHC), which exhibits high biocompatibility and can self-assemble in aqueous solutions. The core-shell structure of the amphiphatic hybrid nanocarrier functions as a physical barrier to regulate drug delivery and decreases drug loss caused by the swelling phenomenon of the polymeric molecules in an aqueous solution.

According to the light or heat sensitivity of the drug, the drug-carrying contact lenses of the present invention can be categorized into the encapsulation-type drug-carrying contact lens and the soaking-type drug-carrying contact lens. The drugs insensitive to light and heat may be used in the encapsulation-type drug-carrying contact lens. The drugs sensitive to light or heat may be used in the drug soaking-type drug-carrying contact lens. The encapsulation-type drug-carrying contact lenses may be further classified into the contact lens wherein the drug molecules are directly mixed with the contact lens material, and the contact lens wherein the drug molecules are sprayed onto the surface thereof to form a drug-containing film. No matter what type the drug-carrying contact lens of the present invention belongs to, it can always achieve the function of gradual and local drug delivery.

Below are described in detail the methods for fabricating various types of the drug-carrying contact lenses of the present invention. Before the methods are described is briefly introduced the amphiphatic organic-inorganic chitosan-silica hybrid nanocarrier used by the present invention.

Refer to FIG. 1 showing the structural formula of the amphiphatic organic-inorganic chitosan-silica hybrid nanocarrier and the self-assembly thereof. The backbone I of chitosan has carboxyl-modified hydrophilic terminals II and long carbon chain-modified hydrophobic terminals III, whereby the chitosan can self-assemblies in an aqueous solution to form a hybrid nanoparticle having a core-shell structure. The method for fabricating the nanocarrier includes steps: dissolving 0.25 g of the amphiphatic organic chitosan having carboxyl-modified hydrophilic terminals and long carbon chain-modified hydrophobic terminals in 50 ml of deionized water, and agitating them at an ambient temperature for 24 hours to form an amphiphatic organic chitosan solution having a concentration of 0.5% wt %; gradually adding 160 μl of APTMS (or APTES) and 0.012 g of EDC to the amphiphatic organic chitosan solution, and agitating them at an ambient temperature for 24 hours to form an organic-inorganic mixture solution, wherein APTMS and APTES respectively denote 3-aminopropyltrimethoxysilane and 3-aminopropyltriethoxysilane and both function as coupling agents of inorganic silanyl groups, and wherein EDC denotes 1-ethyl-3-(3-dimethylaminopropyl)carbodiimide and functions as a catalyst; using an dialysis membrane and a 75 v % alcohol solution to dialysate the organic-inorganic mixture solution for 24 hours, and then using dehydrated alcohol to dialysate the organic-inorganic mixture solution for 24 hours to obtain a dialysated product; drying the dialysated product with an oven to obtain the powder of the amphiphatic organic-inorganic chitosan-silica hybrid nanocarriers (abbreviated as silica-CHC thereinafter) shown in the drawing.

In one embodiment, the method for fabricating the contact lens material includes steps: uniformly mixing HEMA (2-hydroxyethyl methacrylate) with 0.5-5 v % MAA (methacrylate acid) to form a base material; uniformly mixing the HEMA-MAA mixture solution with GDMA (ethylene glycol dimethylacrylate) and AIBN (2,2'-Azobisisobutyronitrile) to form a material of the drug-carrying contact lens in the present invention, wherein GDMA functions as a cross-linking agent and AIBN functions as a photoinitiator. The abovementioned contact lens material is only an exemplification of the contact lens materials used in the present invention. Various contact lens materials available in the market may also be used to fabricate the drug-carrying contact lens according to the present invention.

Figure 2:
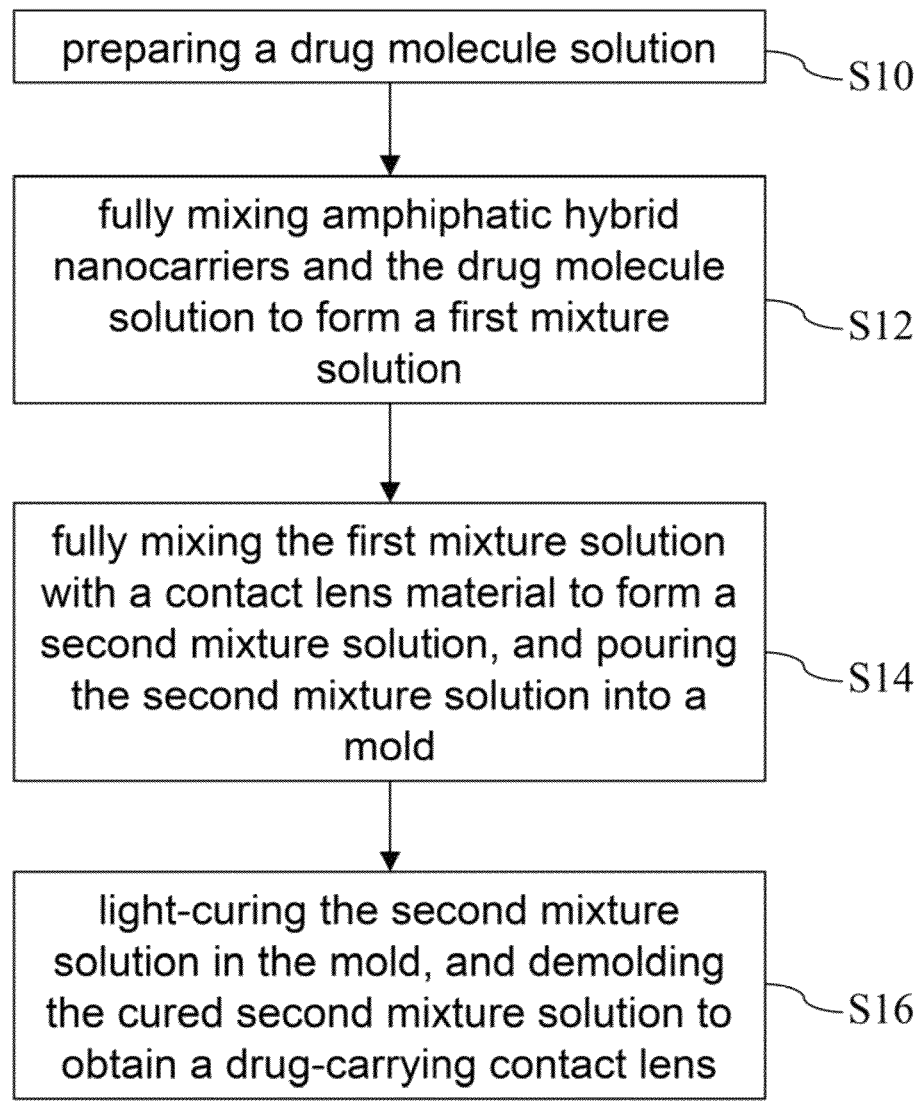
FIG. 2 shows a flowchart of a method for fabricating a first encapsulation-type drug-carrying contact lens according to one embodiment of the present invention.

Refer to FIG. 2 a flowchart of a method for fabricating a first encapsulation-type drug-carrying contact lens according to one embodiment of the present invention. In Step S10, dissolve drug molecules in a polar organic solvent, such as ethanol, PEG (Poly Ethylene Glycol), PPG (Poly Propylene Glycol), DMSO (dimethyl sulfoxide), THF (tetrahydrofuran), or an arbitrary combination thereof, and dilute the organic solution with deionized water to obtain a drug molecule solution having a given concentration. Next, in Step S12, add the silica-CHC powder into the drug molecule solution, and agitate them at an ambient temperature for 24 hours to obtain a first mixture solution. Next, in Step S14, process the first mixture solution centrifugally at a rotation speed of 8000 rpm for 20 minutes, take out the upper layer of the liquid to get the encapsulation rate, and take out the lower layer of the liquid, and mix it with the contact lens material uniformly to form a second mixture solution, and pour the mixture solution into a mold. Next, in Step S16, cure the second mixture solution in the mold with ultraviolet light, demold the cured second mixture solution to obtain a semi-finished product, and flush the semi-product with a buffer solution to remove the unreacted monomers on the surface to obtain a first encapsulation-type drug-carrying contact lens.

Figure 3:
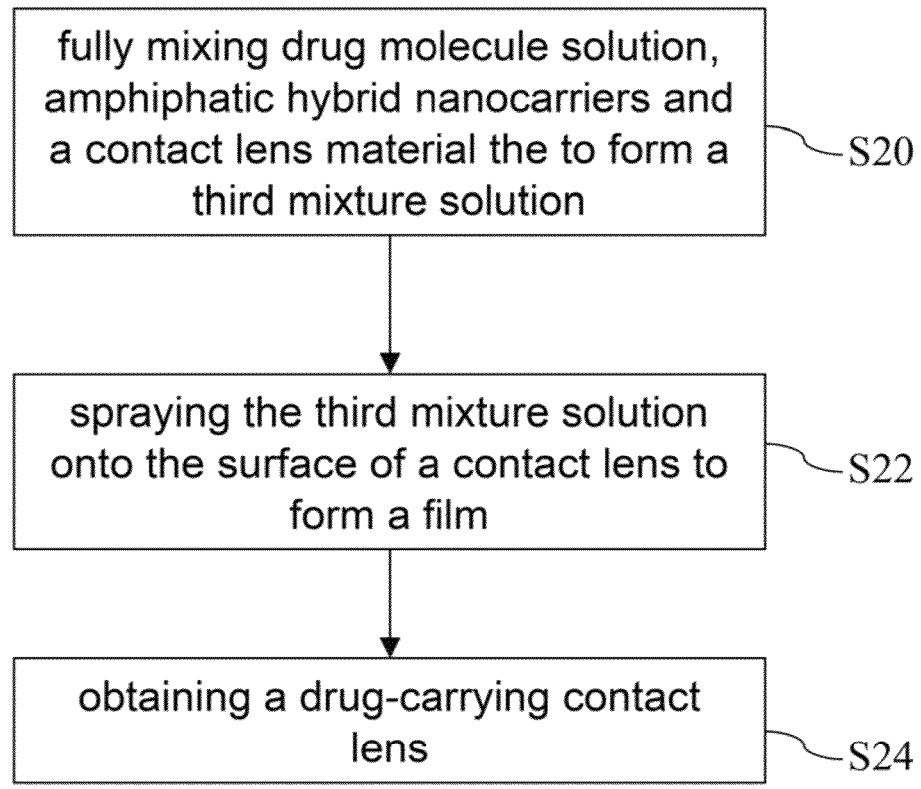
FIG. 3 shows a flowchart of a method for fabricating a second encapsulation-type drug-carrying contact lens according to one embodiment of the present invention.

Refer to FIG. 3 a flowchart of a method for fabricating a second encapsulation-type drug-carrying contact lens according to one embodiment of the present invention. In Step S20, mix uniformly the abovementioned drug molecule solution (the fabrication method thereof has been described hereinbefore and will not repeat here), the amphiphatic hybrid nanocarriers and the polymer of the contact lens material to form a third mixture solution. The polymer contains PHEMA (poly(2-hydroxyethyl methacrylate)) and PMAA (poly(methacrylate acid)) by a ratio of 100:0.5-5, such as the contact lens material mentioned above. Next, in Step S22, spray the third mixture solution onto an existing contact lens to form a film having a thickness of 0.5-10 μm. Thus, the film contains the amphiphatic hybrid nanocarriers carrying drug molecules as a second encapsulation-type drug-carrying contact lens in Step S24.

Figure 4:
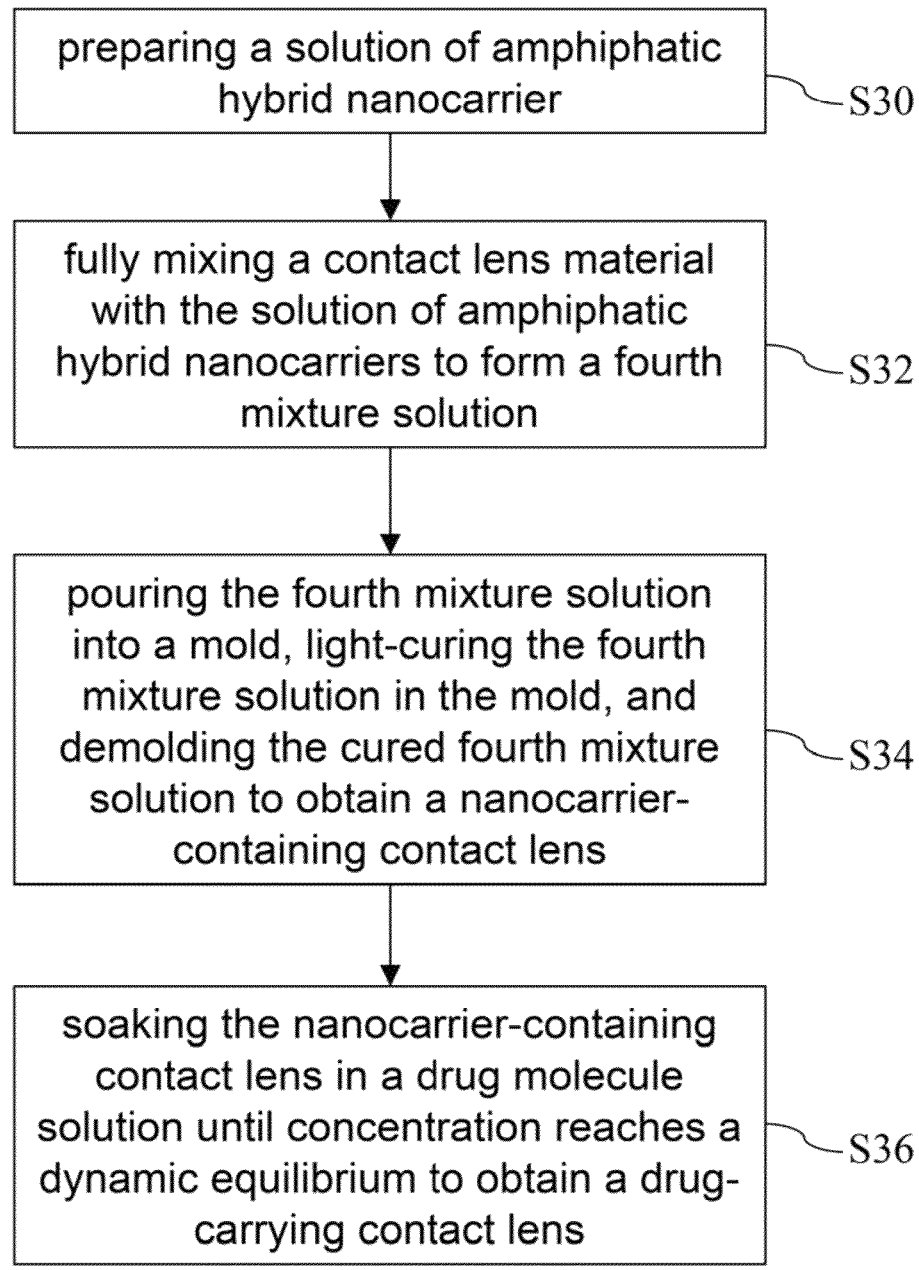
FIG. 4 shows a flowchart of a method for fabricating a drug-soaking type drug-carrying contact lens according to one embodiment of the present invention.

Refer to FIG. 4 a flowchart of a method for fabricating a drug-soaking type drug-carrying contact lens according to one embodiment of the present invention. In Step S30, add the silica-CHC powder into deionized water, and agitate them at an ambient temperature for 24 hours, and process them centrifugally at a rotation speed of 8000 rpm to obtain a solution of the amphiphatic hybrid nanocarriers. Next, in Step S32, take out the lower layer of the amphiphatic hybrid nanocarrier solution, and mix it with the abovementioned contact lens material uniformly to obtain a fourth mixture solution. Next, in Step S34, pour the fourth mixture solution into a mold, cure the fourth mixture solution in the mold with ultraviolet light, demold the cured fourth mixture solution to obtain a semi-finished product, and flush the semi-finished product with a buffer solution several times to remove the unreacted monomers to obtain a nanocarrier-containing contact lens. Next, in Step S36, dissolve the drug molecules in a polar organic solvent or deionized water to obtain a drug molecule solution, and soak the nanocarrier-containing contact lens in the drug molecule solution for 24 hours so that the concentration can reach a dynamic equilibrium, and take out the contact lens to obtain a drug-soaking type drug-carrying contact lens.

Water Retention Test

Figure 5:
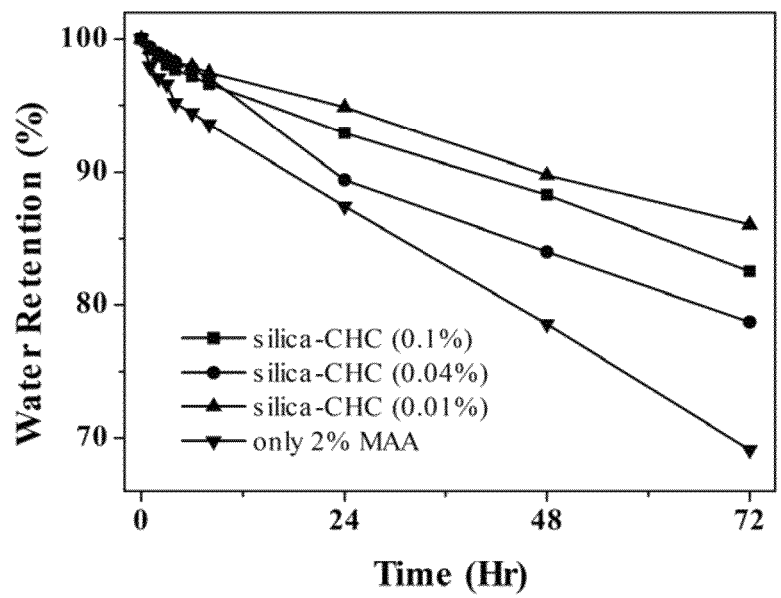
FIG. 5 shows the test result of the water retentions of the drug-carrying contact lenses with respect to the quantities of the nanocarriers added to the contact lenses.

The water retentions of the drug-carrying contact lenses fabricated according to the abovementioned methods are tested with respect to the quantities of the nanocarriers added to the contact lenses. Firstly, dry the nanocarrier-containing contact lens in an oven, weigh the contact lens (Wd), and then soak the contact lens in physiological saline at an ambient temperature for 3 days to saturate the contact lens, dry the surface thereof, and weigh it again (Ww). Next, place the contact lens in an enclosed container, weigh the contact lens periodically (Wt), and obtain the water retention according to the equation: water retention (%)=100%×(Wt−Wd)/(Ww−Wd). The test results are shown in FIG. 5. The MAA monomer is usually added to the ordinary contact lenses to increase the water retention. In addition to the MAA monomer, the drug carriers also play the same role in the present invention. From FIG. 5, it is known that the water retention of the contact lens containing silica-CHC is higher than that of the contact lens containing only MAA by 10-25% (24-72 h). Thus is because the chemical structure of the silica-CHC has many Si—OH groups, which can increase the hydrophilicity and water retention ability.

Drug-Release Test

The drug-release tests are respectively performed on the first encapsulation-type drug-carrying contact lens and the drug-soaking type contact lens of the present invention to understand the drug-release thereof.

Figure 6:
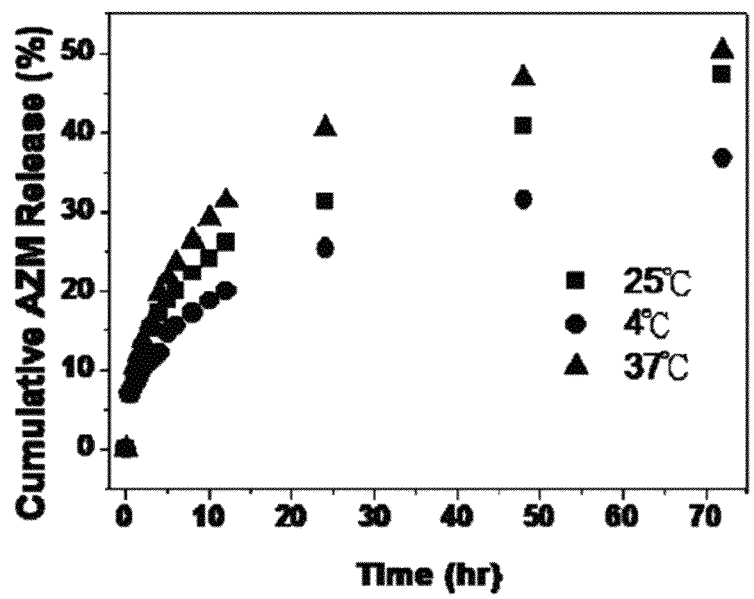
FIG. 6 shows the drug release test result of Azithromycin contained by the encapsulation-type drug-carrying contact lens with respect to the temperature.

In one embodiment, the encapsulation-type drug-carrying contact lens adopts a hydrophobic antibiotic—Azithromycin, which is an oral azalide group antibiotic that is a subgroup of macrolides, and which is a broad-spectrum antibiotic effective to Gram-positive bacteria, Gram-negative bacteria, anaerobic bacteria, Chlamydia, helicoids, etc. The results of the drug-release tests are shown in FIG. 6. FIG. 6 shows that the release quantity of Azithromycin increases with the temperature. Such a phenomenon may be attributed to the fact: the higher the temperature, the higher the oscillation frequency of the drug molecules, and the greater the quantity of the drug molecules diffusing out. In the present invention, the drug-release amount can be quantitively controlled according to the application environment. Therefore, the present invention has a potential to realize a customized drug-carrying contact lens.

Figure 7A:
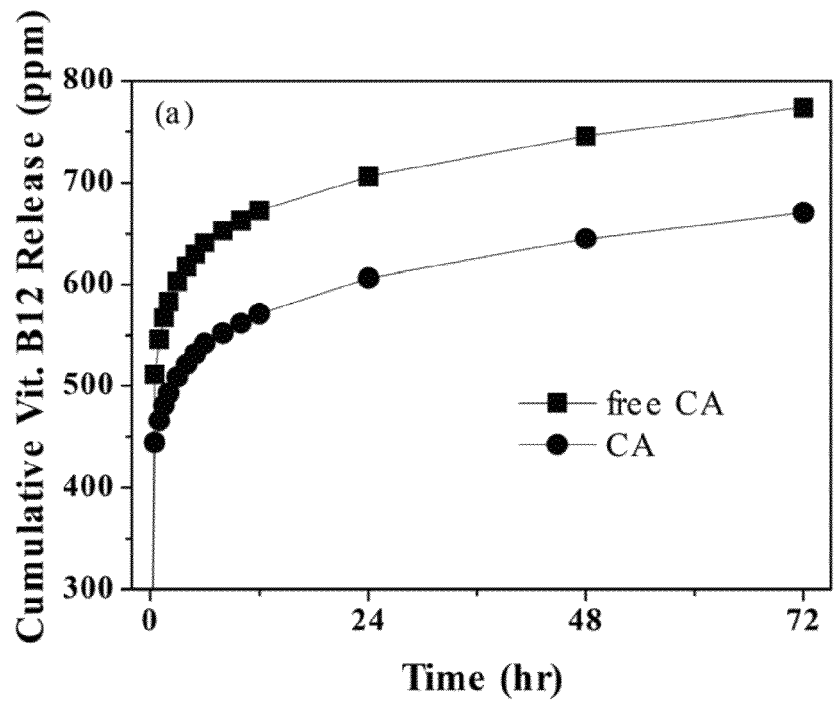
FIG. 7($a$) shows the drug release test result of Vitamin B12 respectively contained by the drug-carrying contact lens containing the drug carriers of the present invention and the drug-carrying contact lens free of drug carriers.
Figure 7B:
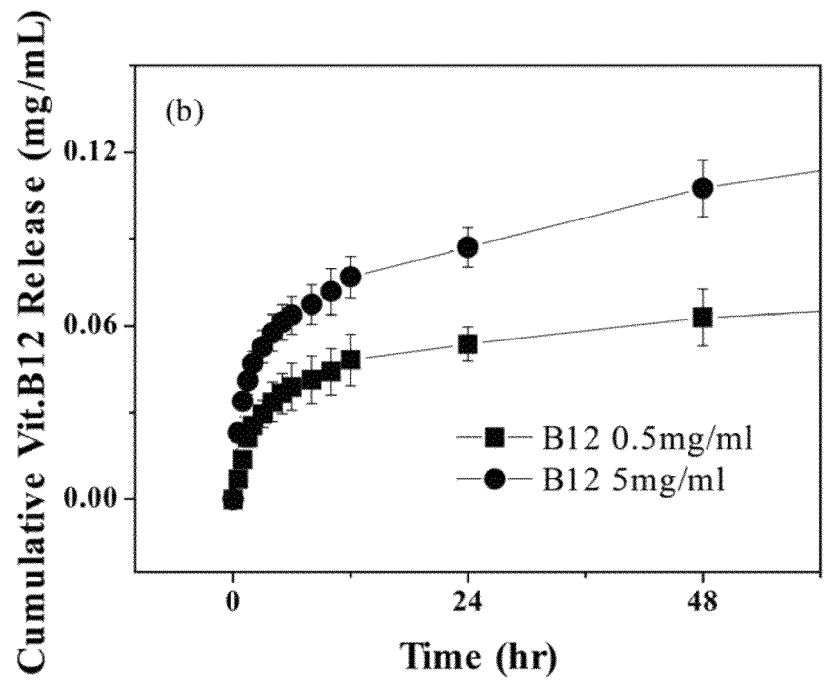

In one embodiment, the drug-soaking type drug-carrying contact lens adopts Vitamin B12, which is a hydrophilic drug and effective to pernicious anaemia, and which is a red crystalline powder likely to absorb humidity, easy to dissolve in water and alcohol, and slightly unstable in the environment of light, strong acid, and base. The results of the drug-release tests are shown in FIG. 7(a) and FIG. 7(b). FIG. 7(a) shows that the drug-carrying contact lens containing the drug carriers of the present invention releases the hydrophilic drug (Vitamin B12) more slowly than the drug-carrying contact lens free of drug carriers. Such a phenomenon is attributed the fact: the porous core-shell structure (with pores of about 2-10 nm according to the BET analysis) of the drug carrier of the present invention effectively reduced the diffusion of the wrapped drug molecules, which is induced by the swelling of polymer in an aqueous solution. FIG. 7(b) shows that the drug-release rate increases with the concentration of the drug molecules. Such a phenomenon is attributed to the fact that the greater the concentration difference, the higher the driving force of drug molecule diffusion.

Image Analysis

Figure 8A:
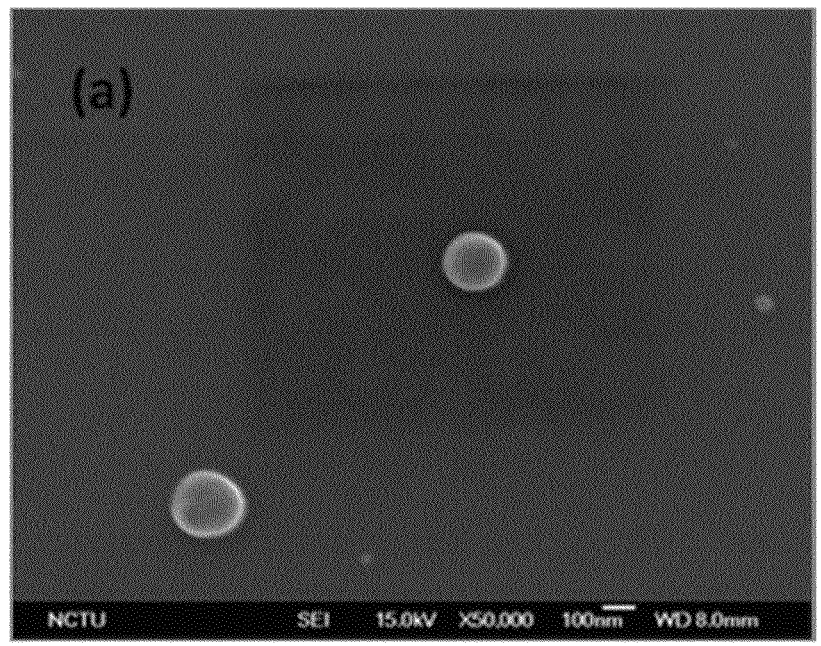
FIG. 8($a$) shows the SEM image of the amphiphatic organic-inorganic chitosan-silica hybrid nanocarriers of the present invention.
FIG. 8(b) shows the SEM image of the drug-carrying contact lens of the present invention.
Figure 8B:
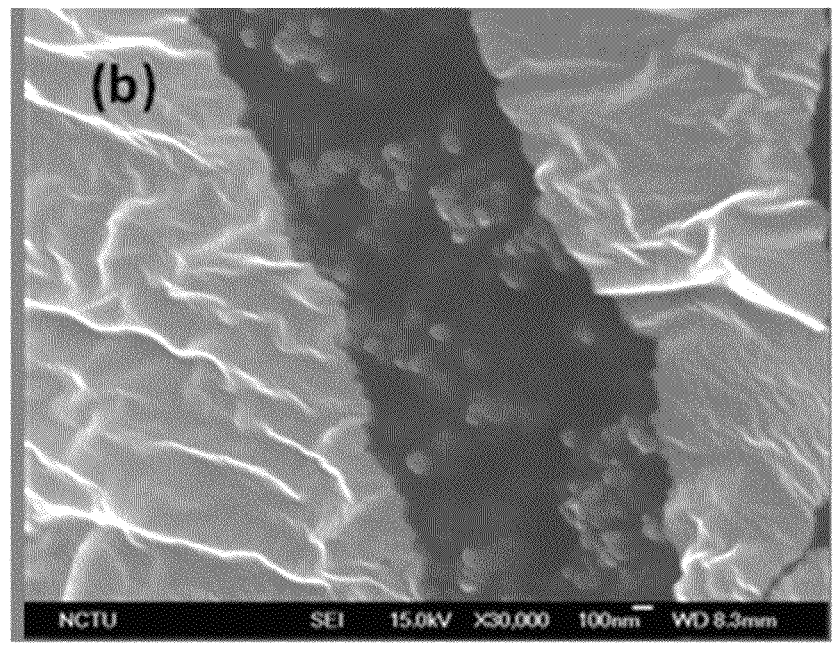

The results of the SEM (Scanning Electron Microscopy) analysis are shown in FIG. 8(a) and FIG. 8(b). FIG. 8(a) shows that the amphiphatic organic-inorganic chitosan-silica hybrid nanocarriers of the present invention are self-assembled in water to form a particle having a diameter of about 100 nm. FIG. 8(b) shows that the amphiphatic organic-inorganic chitosan-silica hybrid nanocarriers are distributed in the drug-carrying contact lens of the present invention.

In conclusion, the present invention uses a highly-biocompatibile nanocarriers having superior drug encapsulation capability to wrap the drug or absorb the drug molecules from the drug solution. Thereby, the drug molecules are uniformly distributed in the contact lens and can be gradually (>24 h) and locally released to the eye of the user wearing the contact lens of the present invention. Therefore, the present invention can prevent or cure ocular diseases with the loss and side effects of the drug being reduced. The present invention is easy to fabricate and thus has wide application.

The embodiments described above are to demonstrate the technical thoughts and characteristics of the present invention and enable the persons skilled in the art to understand, make and use the present invention. However, the embodiments described above are only to exemplify the present invention but not to limit the scope of the present invention. Any equivalent modification or variation according to the spirit of the present invention is to be also included within the scope of the present invention.

What is claimed is:
1. A drug-carrying contact lens comprising:
a contact lens containing at least one amphiphatic hybrid nanocarrier carrying drug molecules, wherein said amphiphatic hybrid nanocarrier is an amphiphatic organic-inorganic chitosan-silica hybrid nanocarrier, and wherein said amphiphatic hybrid nanocarriers and said drug molecules carried thereby are distributed inside said contact lens or on a surface of said contact lens; and a polymeric material, wherein said polymeric material is mixed with said amphiphatic hybrid nanocarriers and said drug molecules to form a mixture solution, and wherein said mixture solution is sprayed onto said surface of said contact lens to form a film, and wherein said polymeric material contains PHEMA ((poly 2-Hydroxy ethylmethacrylate)) and PMAA (poly(methacrylate acid)) by a ratio of 100:0.5-5.

2. The drug-carrying contact lens according to claim 1, wherein said amphiphatic hybrid nanocarrier is an optically transparent nanosphere having a diameter of 20-300 nm.

3. The drug-carrying contact lens according to claim 1, wherein said amphiphatic hybrid nanocarriers have a concentration of 0.01-5% by weight of the total weight of the contact lens.

4. The drug-carrying contact lens according to claim 1, wherein said drug molecule is a hydrophilic or hydrophobic drug molecule.

5. The drug-carrying contact lens according to claim 1, wherein said drug molecule is selected from a group consisting of Vitamin A, Vitamin B12, Vitamin C, Vitamin E, azithromycin, fluorometholone facetate, bacitracin, neomycin, polymyxin B sulfate, Oxytetracycline HCl, erythromycin, dexamethasone, prednisolone acetate, timolol maleate, and hydrocortisone.

\* \* \* \* \*